United States Patent [19]
Shalaby et al.

[11] 4,226,243
[45] Oct. 7, 1980

[54] SURGICAL DEVICES OF POLYESTERAMIDES DERIVED FROM BIS-OXAMIDODIOLS AND DICARBOXYLIC ACIDS

[75] Inventors: Shalaby W. Shalaby, Lebanon; Dennis D. Jamiolkowski, Long Valley, both of N.J.

[73] Assignee: Ethicon, Inc., Somerville, N.J.

[21] Appl. No.: 61,339

[22] Filed: Jul. 27, 1979

Related U.S. Application Data

[62] Division of Ser. No. 905,325, May 12, 1978.

[51] Int. Cl.$^3$ .................. A61L 17/00; A61F 1/00
[52] U.S. Cl. ...................................... 128/335.5; 3/1
[58] Field of Search .......................... 128/335.5; 3/1

[56] References Cited

U.S. PATENT DOCUMENTS

| | | |
|---|---|---|
| 3,773,737 | 11/1973 | Goodman et al. .......... 128/335.5 |
| 4,032,993 | 7/1977 | Coquard et al. .......... 128/335.5 |
| 4,105,034 | 8/1978 | Shalaby et al. .......... 128/335.5 |
| 4,113,851 | 9/1978 | Leveen .......... 128/335.5 |
| 4,140,678 | 2/1979 | Shalaby et al. .......... 128/335.5 |
| 4,141,087 | 2/1979 | Shalaby et al. .......... 128/335.5 |

*Primary Examiner*—Robert W. Michell
*Assistant Examiner*—Thomas Wallen
*Attorney, Agent, or Firm*—Wayne R. Eberhardt

[57] ABSTRACT

Alternating esteramide polymers are obtained from the reaction of bis-oxamidodiols such as N,N'-bis($\omega$-hydroxyalkylene)oxamide with a dicarboxylic acid or diesters such as diethyl oxalate, diethyl succinate, diethyl suberate, or dimethyl terephthalate. The polymers are obtained in good yield and have film- and fiber-forming properties. Some polymers are absorbable in biological systems and are useful as absorbable surgical devices. Other of these polymers are nonabsorbable and are useful as textile fibers.

17 Claims, No Drawings

SURGICAL DEVICES OF POLYESTERAMIDES DERIVED FROM BIS-OXAMIDODIOLS AND DICARBOXYLIC ACIDS

This is a division, of application Ser. No. 905,325, filed May 12, 1978.

BACKGROUND OF THE INVENTION

1. Field of the Invention

The present invention relates to alternating esteramide polymers, and more particularly, to polyesteramides derived from bis-oxamidodiols and dicarboxylic acids or their diesters.

2. Description of Prior Art

Polyesters and polyamides are well-known thermoplastic heterochain polymers, and polyesteramides have been studied as a hybrid of these two basic polymers. U.S. Pat. No. 3,493,544, for example, describes the preparation of a random polyesteramide copolymer by reacting diamines and diacids in the presence of a lactone. U.S. Pat. No. 3,493,632 discloses the preparation of block polyesteramides by heating a mixture of a polyester and a polyamide to a temperature intermediate the glass transition temperatures and melting temperatures of the two polymers.

Other reports in the literature disclose the preparation of polyesteramides by reacting a bis-esteramide with a diol [Europ. Polym. J. 12, 585 (1976), Polymer 16, 565 (1975)], a diamidediol with a dicarboxylic acid [J. Appl. Polym. Sci. 20, 975 (1976)], an ω-aminoalcohol or aminophenol with a diacid [Bull Soc. Chim. (France), 2264 (1971), Fr. Pat. No. 2,016,340], an ethanolamine with an oxalic ester [J. Agr. Chem. Soc., Japan 18, 54, 76 (1972); Chem. Abs. 45, 2214g, 2215a (1951)], and an aminoisopropanol with oxalic acid [J. Agr. Chem. Soc., Japan 19, 805 (1943); Chem. Abs. 45, 8777e (1951)].

Bis-amide diols derived from $C_2$ to $C_4$ aminoalcohols have also been disclosed in the art [J. Chem. Soc., 2006-10 (1956); Chem. Abs. 51, 262d (1957), Plaste u. Kautschuk 6, 372-75 (1959); Chem. Abs. 54, 6180e (1960)]. None of the prior art references, however, disclose the reaction of bis-oxamidodiols with dicarboxylic acids to obtain the novel polyesteramides of the present invention.

It is accordingly an object of the present invention to provide new, alternating polyesteramides derived from the reaction of bis-oxamidodiols with a dicarboxylic acid or diester. It is a yet further object of this invention to provide new polyesteramides which are susceptible to hydrolysis and useful in the preparation of absorbable sutures and other surgical devices. Another object of this invention is to provide hydrolytically stable, fiber-forming polyesteramide polymers useful in the preparation of nonabsorbable surgical sutures and textile fibers. These and other objects of the invention will be apparent from the ensuing description and claims.

SUMMARY

Bis-oxamidodiols represented by the formula

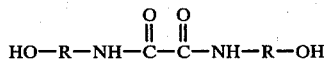

wherein R is a divalent aliphatic or aromatic hydrocarbon radical having from 3 to about 8 carbon atoms, are condensed with a dicarboxylic acid ester, optionally in the presence of a volatile alkanediol to form alternating polyesteramides of the formula

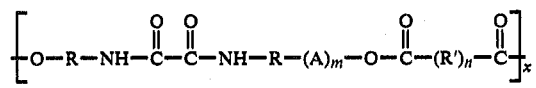

wherein R is as above defined, R' is a divalent aliphatic or aromatic hydrocarbon radical having from 1 to about 8 carbon atoms, A is a divalent oxyalkyl radical derived from the alkanediol, m is 0 or 1, n is 0 or 1, and x is the degree of polymerization resulting in a film-forming or fiber-forming polymer.

Polyesteramides derived from bis-oxamidodiols and dialkyl oxalate are absorbable in living animal tissue and are particularly useful in the preparation of absorbable surgical sutures and other devices.

DESCRIPTION OF PREFERRED EMBODIMENTS

Bis-oxamidodiols useful in the preparation of the polyesteramides of the present invention are prepared by reacting diethyl oxalate with an amino-alcohol in dry methanol under oxygen-free conditions as hereinafter described in detail. The resulting compounds are represented by the formula

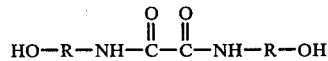

wherein R is a divalent aliphatic or aromatic hydrocarbon radical having from 3 to about 8 carbon atoms, preferably selected from the group consisting of alkylene, cycloaliphatic, alkylenecycloaliphatic, aryl and alkary. Particularly preferred hydrocarbon radicals include $C_{3-8}$ alkylene, $-CH_2-C_6H_{10}-CH_2-$, phenylene and methylenephenylene.

The bis-oxamidodiols of the present invention are condensed with a dicarboxylic acid ester to obtain an alternating polyesteramide having film- and fiber-forming properties. Preferred dicarboxylic acid esters are the dialkyl esters of oxalic, succinic, suberic, and terephthalic acids, and the diethyl, dimethyl, and dibutyl esters of such acids are particularly preferred.

The polymerization reaction may optionally be conducted in the presence of a volatile diol, preferably a $C_4$ to $C_8$ alkanediol, in order to increase the molecular weight of the esteramide polymer. Polymers thus prepared may contain up to about 10 mole percent of the alkane diol radical in the polymer chain.

Polyesteramides derived from oxalate esters are sensitive to hydrolysis and are useful in the fabrication of absorbable surgical devices and in the preparation of implantable, slow release drug delivery compositions. Polyesteramides based on succinate, suberate and terephthalate esters are moisture resistant and useful in the preparation of nonabsorbable surgical sutures and textile fibers. The terephthalate polyesteramide in particular has chemical and physical properties such as high degree of pliability, good dyeing characteristics and good dimensional stability which make it especially attractive for use as a textile fiber.

The preparation and properties of the new polyesteramide polymers of the present invention will be more clearly understood from the following examples which are presented by way of illustration and are not limitating of the present invention.

The following analytical methods were used to obtain the data reported in the examples. Inherent viscosity ($\eta$inh) was obtained on polymer solutions (1 gram/liter) in hexafluoroisopropanol (HFIP) at 25° C. The infrared spectra of polymer films (cast from HFIP) were recorded on a Beckman Acculab 1 spectrophotometer. The NMR spectra of the polymer solutions in $CDCl_3$ were recorded on an MH-100 or CFT-20 spectrophotometer. A DuPont 990 DSC apparatus was used to record the glass transition (Tg), crystallization (Tc) and melting temperatures (Tm) of the polymers under nitrogen, using about 5 mg samples and a heating rate of 10° C./min or 20° C./min as specified in the example. Crystallinity was determined by the method of Hermans and Weidinger and the diffractometer patterns were resolved with a DuPont 310 curve analyzer.

In vitro hydrolysis of polymer discs (about 1.2 g, 2.2 cm diameter) and monofilaments (7–25 mil) was conducted at 37° C. in phosphate buffer comprising a solution of 27.6 g sodium dihydrogenphosphate monohydrate in 1000 ml water adjusted to pH 7.25 with sodium hydroxide.

In vivo absorption (subcutaneous) was determined by implanting two segments of suture, 2 cm long, into the abdominal subcutis of young female rats. The implants were readily visible when the skin was wetted with propylene glycol and extent of absorption was determined by subjective visual examination.

EXAMPLE I

Preparation of
N,N'-bis(3-hydroxytrimethylene)oxamide

3-Amino-1-propanol (225 g, 3 mole) was dissolved in dry methanol (500 ml). To this was added distilled diethyl oxalate (219 g, 1.5 mole) during 0.5 hr. The addition rate allowed the reaction to proceed under a gentle reflux. After the addition was completed, the reaction mixture was stirred, without any external heating, for about one hour. The precipitated product was isolated by filtration and washed with a 1:1 mixture of ether and methanol. The product was dried in vacuo at 25° C. to give an almost quantitative yield, m.p. 159°–160° C.

The IR, NMR, and elemental analysis data of a pure sample recrystallized from methanol was consistent with the proposed structure.

EXAMPLE II

Preparation of
N,N'-bis(5-hydroxypentamethylene)oxamide

A solution of distilled diethyl oxalate (37.6 g, 0.267 mole) in dry methanol (35 ml) was added slowly under dry and oxygen-free conditions to a magnetically stirred solution of distilled 5-amino-1-pentanol (52.0 g, 0.504 mole) in dry methanol (325 ml). The glass apparatus containing the amino-alcohol solution was immersed in cold water so that the addition, which was completed in 3.5 hrs, was carried out at or slightly below room temperature. After the addition was completed, the reaction mixture was allowed to stir at room temperature for 3 days. A stream of nitrogen was passed over the mixture concentrating it to a total volume of about 350 ml. A white solid was recovered from the cooled mixture by filtration. The solid was washed with a portion of methanol (100 ml) at room temperature followed by two washings of chilled methanol (100 ml portions each) and dried in vacuo to give the product in 88% yield (57.6 g, 0.221 mole), m.p. 155° C. The product was recrystallized from distilled water (10 ml $H_2O$/g solute) and the resulting solid washed with a small quantity of carbon tetrachloride. The purified product was dried in vacuo, m.p. 155°–156° C.

EXAMPLE III

Preparation of
N,N'-bis(6-hydroxyhexamethylene)oxamide

A solution of distilled diethyl oxalate (150 g, 1.03 mole) in dry methanol (350 ml) was added slowly under dry and oxygen-free conditions to a mechanically stirred solution of distilled 6-amino-1-hexanol (205 g, 1.75 mole) in dry methanol (800 ml). The glass apparatus containing the amino-alcohol solution was immersed in cold water prior to the start of the addition so that the process was carried out at or slightly below room temperature. The rate of addition was adjusted to about 75 ml/hr with all but 250 ml of the oxalate solution being added with stirring. The mixture was stirred for 24 hours after which the addition was completed at a rate of about 100 ml/hr. The precipitate was filtered, washed with methanol three times, followed by a single ether wash. The product (227.8 g, 90% yield) had a m.p. of 161°–162° C.

EXAMPLE IV

Preparation of Poly N,N'-bis(trimethylene)oxamido oxalate

N,N'-bis(3-hydroxytrimethylene)oxamide (2.04 g, 10 mmole), dibutyl oxalate (2.04 g, 10 mmole) and a catalytic amount of Tyzor TOT* (0.012 M in toluene—0.1 ml, 0.0012 mmole) were transferred under dry, oxygen-free conditions into a glass reactor equipped for magnetic stirring. The mixture was heated at 155°–160° C. for 4 hours under $N_2$ at 760 torr. The polymerization was then continued under reduced pressure according to the following scheme: 160° C./2 hrs/0.2 torr, 170/1/0.2, 180/1/0.2 and 190/2/0.2. The polymer was isolated, ground and dried in vacuo.

*Tyzor TOT: a tetralkyl titanate catalyst manufactured by E. I. du Pont de Nemours & Co., Wilmington, Del. 19898.

A sample of the polymer was analyzed. NMR and IR data were consistent with the proposed structure. Other data were as follows:
Inherent viscosity: 0.26
DSC (10° C./min)
    Initial: Tg=47, Tc=62, Tm=173° C.
    Reheating: Tg=44, Tc=72, Tm=173° C.
In vitro hydrolysis-(2.2 cm dia.×1.9 cm thick disk)
    16% weight loss after 3.5 days
    75% weight loss after 8.5 days

EXAMPLE V

Preparation of Poly N,N'-bis(pentamethylene)oxamido oxalate (A)

N,N'-bis(5-hydroxypentamethylene)oxamide (5.0 g, 19.2 mmole), diethyl oxalate (2.7 g, 18.5 mmole) and stannous octoate (0.028 ml of a 0.33 M solution in toluene, 0.0092 mmole) were added under dry and oxygen-free conditions to a glass reactor equipped for magnetic stirring. The mixture was heated at 140, 150, and 160° C. for 2.5, 0.75, and 4 hours, respectively, while under one atmosphere. The polymerization was continued under reduced pressure (0.1 torr) by heating at 160° to 185° C.

for 4.6 hours. The polymer was isolated, ground, and dried in vacuo and characterized as follows:
Inherent viscosity: 0.22
DSC (10° C./min)
  Initial: Tm=166° C.
  Reheating: Tm=162° C.
IR: data was consistent with proposed structure
In vitro hydrolysis—(2.2 cm dia. disk, 1.1 g in weight) 73% weight loss after 27 days (B)

In order to improve the obtainable molecular weight, the reaction of (A) was repeated with a more volatile diol, 1,6-hexanediol, added to the reaction mixture as the excess component; analysis shows that subsequent polymerization incorporates a small amount of this material (as —O(CH$_2$)$_6$O—) into the polymer.

N,N'-bis(5-hydroxypentamethylene)oxamide (6.300 g, 24.19 mmole), 1,6-hexanediol (0.208 g, 1.76 mmole), diethyl oxalate (3.645 g, 24.94 mmole) and a catalytic amount of (CH$_3$)$_3$($\phi$CH$_2$)NHTi(OBu)$_6$ (0.005 ml of a 0.2 M solution in n-butanol, 0.001 mmole) were added to a glass reactor equipped for magnetic stirring. After purging the reactor to ensure dry and oxygen-free conditions, the polymerization was begun by heating to 140° C. under N$_2$ at one atmosphere while collecting the formed ethanol. The polymerization was characterized by the collection of excess and formed alcohols, and was conducted according to the following scheme: 140° C./3 hrs/760 torr (N$_2$), 160/2/760, 180/1/0.03, 190/2/0.03 and 215/5/0.03. The polymer was isolated, ground, and dried in vacuo.
Inherent viscosity: 0.77
DSC (20° C./min)
  Initial: Tm=172° C.
  Reheating: Tc=42, TM=171° C.

EXAMPLE VI

Preparation of Poly N,N'-bis(hexamethylene)oxamido oxalate (A)

N,N'-bis(6-hydroxyhexamethylene)oxamide (5.0 g, 17.4 mmole) and diethyl oxalate (2.46 g, 16.84 mmole) were added to a glass reactor equipped for magnetic stirring under dry and oxygen-free conditions. The vessel was heated under nitrogen at one atmosphere at 170° C. for 4 hours. The pressure was reduced to 0.1 torr and the polymerization continued by heating at 170, 190, and 200° C. for 4, 1.5, and 2.5 hours, respectively, while removing excess and formed alcohols. The polymer was isolated, ground, dried in vacuo and characterized as follows:
Inherent viscosity: 0.85
DSC (10° C./min)
  Initial: Tm=172° C.
  Reheating: Tg=33° C., Tm=170° C.

(B)

In order to improve the obtainable molecular weight, the reaction of (A) was repeated with a more volatile diol, 1,6-hexanediol, added to the reaction mixture as the excess component; analysis shows that subsequent polymerization incorporates a small amount of this material (as —O(CH$_2$)$_6$O—) into the polymer.

N,N'-bis(6-hydroxyhexamethylene)oxamide (14.4 g, 0.05 mole), 1,6-hexanediol (1.18 g, 0.01 mole), diethyl oxalate (7.3 g, 0.05 mole) and a catalytic amount of Tyzor TOT (0.3 ml of a 1% solution in toluene) were mixed under dry, oxygen-free conditions. A glass reactor equipped for magnetic stirring was used to conduct the polymerization. The reaction scheme is summarized as follows: 150° C./1 hr/760 torr (N$_2$), 145/16/760, 145/2/0.1, 160/16/0.01, 175/5/0.01, 170/2/0.01, 190/18/0.01 and 200/18/0.01. The polymer was isolated, ground, dried in vacuo and characterized as follows:
Inherent viscosity: 1.51
DSC (10° C./min)
  Initial: Tg=50, Tm=168° C.
  Reheating: Tg=41, Tm=165° C.

The polymer was melt-spun and hand-drawn to obtain fibers having the properties shown below:
Inherent viscosity: 0.97
Crystallinity: 14%
Physical data:
  Diameter=7.25 mils
  Straight tensile strength=24,200 psi
  Elongation=15%
In vivo absorption (subcutaneous): The bulk of the implanted fiber appeared to absorb between 9 and 14 weeks. Fragments of fiber were observed after 20 weeks.
In vitro hydrolysis: Monofilament. 23% weight loss after 77 days.

(C)

N,N'-bis(6-hydroxyhexamethylene)oxamide (23.07 g, 80 mmole), distilled 1,6-hexanediol (2.00 g, 16.9 mmole), distilled diethyl oxalate (13.75 g, 94.1 mmole), and a catalytic amount of (CH$_3$)$_3$($\phi$CH$_2$)NHTi(OBu)$_6$ [0.019 ml of a 0.2 M solution in n-butanol, 0.0038 mmole) were added to a glass reactor equipped for mechanical stirring. After purging the reactor to ensure dry and oxygen-free conditions, the polymerization was begun by heating to 155° C. under N$_2$ at 760 torr while collecting the formed ethanol. The polymerization was characterized by the collection of excess and formed alcohols and was conducted according to the following scheme: 155° C./5 hrs/760 torr (N$_2$), 190/3/0.03, 215/5/0.03. The ivory-colored polymer was isolated, ground and dried in vacuo at room temperature. NMR data was consistent with a structure containing 5.2% 1,6-hexanediol residues (as —O(CH$_2$)$_6$O—) while GC analysis after chemical hydrolysis of the polymer detected 4.2%. IR data was consistent. Other data were as follows:
Inherent viscosity: 0.8
DSC (20° C./min)
  Initial: Tm=170° C.
  Reheating: Tm=167° C.
Crystallinity: 14%

The polymer was melt-spun and drawn to obtain monofilaments having the properties shown below:
Diameter: 7.2 mils
Straight tensile strength: 56,500 psi
Knot tensile strength: 41,800 psi
Elongation at break: 29%

The above monofilaments were annealed under tension at 82° C. for 5 hours to obtain the following properties:
Diameter: 7.0 mils
Straight tensile strength: 62,200 psi
Knot tensile strength: 43,800 psi
Elongation at break: 21%
Young's modulus: 529,000 psi

EXAMPLE VII

Preparation of Poly N,N'-bis(hexamethylene)oxamido succinate

N,N'-bis(6-hydroxyhexamethylene)oxamide (13.0 g, 45 mmole), diethyl succinate (7.7 g, 44 mmole) and stannous oxalate (9 mg, monomer/catalyst=1000), were mixed under dry, oxygen-free conditions in a glass reactor equipped for mechanical stirring. The polymerization scheme was as follows: 160° C./12 hrs/760 torr ($N_2$) and 200/5/0.1. The polymer was isolated, ground and dried in vacuo. The inherent viscosity of this polymer was 0.64. Solid-state post-polymerization of 2 mm particles at 152° C. for 12 and 24 hours resulted in polymers having the following properties:

| Post-polymerization | 12 hrs | 24 hrs |
|---|---|---|
| Inherent viscosity | 0.81 | 0.91 |
| DSC (20° C./min) Initial Tm | — | 168 |
| Reheating Tm | — | 162 |
| % Crystallinity | 48 | — |

EXAMPLE VIII

Preparation of Poly N,N'-bis(hexamethylene)oxamido suberate

N,N'-bis(6-hydroxyhexamethylene)oxamide (12.1 g, 42 mmole) diethyl suberate (9.5 g, 41 mmole) and stannous oxalate (8.5 mg, monomer/catalyst=1000) were mixed under dry, oxygen-free conditions in a glass reactor equipped for magnetic stirring. The polymerization scheme was as follows: 165° C./16 hrs/760 torr ($N_2$), 200/5/0.1, 190–200/4/0.1. The polymer was isolated, ground into 2 mm particles and dried in vacuo. This product, which was shown to have an inherent viscosity of 0.49, was post-polymerized in the solid state at 115° C. for 16 hours and then at 120° C. for 4 hours to give a polymer having an inherent viscosity of 0.56, Tm=144° C. (DSC 20° C./min), and crystallinity=40%. NMR, IR, and elemental analysis data were consistent with the proposed structure.

EXAMPLE IX

Preparation of Poly N,N'-bis(hexamethylene)oxamido terephthalate

N,N'-bis(6-hydroxyhexamethylene)oxamide (8.93 g, 31 mmole), dimethyl terephthalate (5.82 g, 30 mmole) and a catalytic amount of Tyzor OG* (0.078 mmole), 0.36 ml of a 0.216 M solution in toluene) were mixed under dry, oxygen-free conditions, in a glass reactor equipped for magnetic stirring. The polymerization was conducted by heating while stirring (whenever the melt viscosity permitted) according to the following scheme: 190° C./3 hrs/760 torr ($N_2$), 230/2/0.05 and 245/4/0.05.

*Tyzor OG: a tetraoctylene glycol titanate catalyst manufactured by E. I. du Pont de Nemours and Co., Wilmington, Del., 19898.

The polymer was isolated, ground and dried in vacuo. The inherent viscosity was determined to be 2.0. Extrusion of the polymer at 260° C. resulted in a monofilament having an inherent viscosity of 1.46. The monofilaments were hand-drawn (6X) in a silicon oil bath at 200° C. and then annealed under tension at 150° C. for 1 hour. The properties of the annealed and unannealed fibers are summarized below:

|  | Unannealed | Annealed |
|---|---|---|
| Fiber diameter | 12 mils | 12 mils |
| Straight tensile str., psi | 52 | 58 |
| % Elongation | ~5 | ~5 |
| % Crystallinity | 21 | 23 |
| DSC (20° C./min) Initial Tg | 58 | — |
| Reheating Tm | 221 | — |

The esteramide polymers of the present invention are useful in the preparation of both absorbable and nonabsorbable filaments which in turn are useful as surgical sutures. Such sutures may be of either multifilament or monofilament construction, and multifilament sutures are preferably braided although twisted, and covered constructions may also be used. For use as sutures, it is necessary that the fibers be sterilized by exposure to ethylene oxide or other suitable means, and thereafter packaged in a sterile condition ready for use. Moisture sensitive sutures should, of course, be packaged in hermetically sealed, moisture-free containers in accordance with standard practice for such materials.

Filaments of the present invention may also be woven, braided, or knitted alone or in combination with absorbable fibers such as poly(alkylene oxalate), polyglycolide or poly(lactide-co-glycolide), and/or in combination with nonabsorbable fibers such as nylon, polypropylene, poly(ethylene terephthalate), or polytetrafluoroethylene to form multifilament sutures, fabrics, and tubular structures having use in the surgical repair of arteries, veins, ducts, internal organs and the like.

The polymers of the present invention are also useful in the manufacture of cast films and other solid surgical aids such as scleral buckling prostheses. Thus, cylindrical pins, screws, reinforcing plates, and the like, may be cast or machined from solid polymers having various in vivo absorption characteristics depending upon the polymer composition.

Many different embodiments of this invention will be apparent to those skilled in the art and may be made without departing from the spirit and scope thereof. It is accordingly understood that this invention is not limited to the specific embodiments thereof except as defined in the appended claims.

What is claimed is:

1. A surgical suture comprising an oriented filament of an alternating esteramide polymer having repeating units represented by

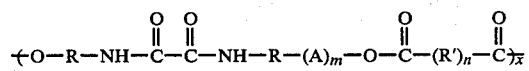

wherein R is a divalent aliphatic or aromatic hydrocarbon radical having from 3 to about 8 carbon atoms, R' is a divalent hydrocarbon radical having from 1 to about 8 carbon atoms, A is a divalent oxyalkylene radical having from 4 to 8 carbon atoms, m is 0 or 1, n is 0 or 1, and x is the degree of polymerization resulting in a film-forming or fiber-forming polymer.

2. A suture of claim 1 wherein R is selected from the group consisting of alkylene, cycloalkylene, alkylene cycloalkylene, arylene, and alkylarylene.

3. A suture of claim 2 wherein the polymer is poly N,N'-bis(hexamethylene)oxamido suberate.

4. A suture of claim 1 wherein n is 0.

5. A suture of claim 4 wherein R is $C_3$ to $C_8$ alkylene, $C_6$ to $C_8$ cycloalkylene or alkylarylene.

6. A suture of claim 4 wherein said polymer is poly N,N'-bis(trimethylene)oxamido oxalate.

7. A suture of claim 4 wherein said polymer is poly N,N'-bis(pentamethylene)oxamido oxalate.

8. A suture of claim 4 wherein said polymer is poly N,N'-bis(hexamethylene)oxamido oxalate.

9. A suture of claim 1 wherein m is 1 and A is —O—(CH$_2$)$_6$—.

10. A suture of claim 1 wherein n is 1 and R' is C$_{1-6}$ alkylene or C$_6$H$_4$ arylene.

11. A suture of claim 1 wherein n is 1 and R' is —(CH$_2$)$_2$—.

12. A suture of claim 11 wherein the polymer is poly N,N'-bis(hexamethylene)oxamido succinate.

13. A suture of claim 1 wherein n is 1 and R' is —(CH$_2$)$_6$—.

14. A suture of claim 1 wherein n is 1 and R' is the p-phenylene divalent radical.

15. A suture of claim 14 wherein the polymer is poly N,N'-bis(hexamethylene)oxamido terephthalate.

16. A surgical prosthesis comprising a sterile fabric composed at least in part of filaments of an alternating esteramide polymer having repeating units represented by

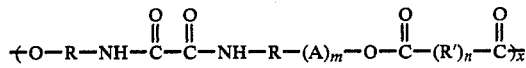

wherein R is a divalent aliphatic or aromatic hydrocarbon radical having from 3 to about 8 carbon atoms, R' is a divalent hydrocarbon radical having from 1 to about 8 carbon atoms, A is a divalent oxyalkylene radical having from 4 to 8 carbon atoms, m is 0 or 1, n is 0 or 1, and x is the degree of polymerization resulting in a film-forming or fiber-forming polymer.

17. A surgical prosthesis comprising a solid surgical aid cast or machined from an alternating esteramide polymer having repeating units represented by

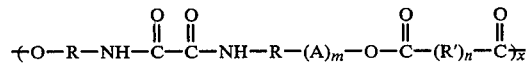

wherein R is a divalent aliphatic or aromatic hydrocarbon radical having from 3 to about 8 carbon atoms, R' is a divalent hydrocarbon radical having from 1 to about 8 carbon atoms, A is a divalent oxyalkylene radical having from 4 to 8 carbon atoms, m is 0 or 1, n is 0 or 1, and x is the degree of polymerization resulting in a film-forming or fiber-forming polymer.

* * * * *